United States Patent [19]

Kurtz et al.

[11] Patent Number: 4,883,476
[45] Date of Patent: Nov. 28, 1989

[54] DRAINAGE DEVICE WITH DISPOSABLE COLLECTION CHAMBER

[75] Inventors: Leonard D. Kurtz, Woodmere; Joseph LiCausi, Port Jefferson Station, both of N.Y.

[73] Assignee: BioResearch, Inc., Farmingdale, N.Y.

[21] Appl. No.: 141,518

[22] Filed: Jan. 7, 1988

[51] Int. Cl.⁴ .............................................. A61M 1/00
[52] U.S. Cl. ...................................... 604/323; 604/319
[58] Field of Search ................ 137/205; 604/318, 319, 604/320, 321, 323, 335, 350; 422/168

[56] References Cited

U.S. PATENT DOCUMENTS

| | | | |
|---|---|---|---|
| 3,363,626 | 1/1968 | Bidwell et al. | 128/276 |
| 3,704,709 | 12/1972 | Sorenson et al. | 604/319 |
| 3,847,152 | 11/1974 | Schachet | 604/321 |
| 3,924,624 | 12/1975 | Schachet | 128/321 |
| 4,105,031 | 8/1978 | Kurtz et al. | 128/276 |
| 4,419,093 | 12/1983 | Deaton | 604/49 |
| 4,439,190 | 3/1984 | Protzmann et al. | 604/319 |
| 4,533,353 | 8/1985 | Akiyama | 604/321 |
| 4,544,370 | 10/1985 | Elliot et al. | 604/319 |
| 4,569,674 | 2/1986 | Phillips et al. | 604/119 |
| 4,605,400 | 8/1986 | Kurtz | 604/318 |
| 4,715,856 | 12/1987 | Elliot et al. | 604/319 |
| 4,747,843 | 5/1988 | Felix et al. | 604/318 |

OTHER PUBLICATIONS

Condensed Chemical Dictionary, Van Nostrand and Co., Inc., New York, N.Y., 10020, 502, 503, 1981.

Primary Examiner—Jerome L. Kruter
Attorney, Agent, or Firm—Larson and Taylor

[57] ABSTRACT

A drainage device is provided with a disposable collection chamber which is attachable to a nondisposable section. The nondisposable section of the drainage device includes the suction control regulator and a valve to prevent admission of atmospheric air to the collection chamber. A receptacle is provided in the nondisposable section to indicate contamination of the nondisposable section in the event liquid from the collection chamber flows into the nondisposable section. A liquid biocidal chamber is provided in the collection chamber to prevent contaminates and infectious material from passing from the collection chamber into the nondisposable section.

8 Claims, 2 Drawing Sheets

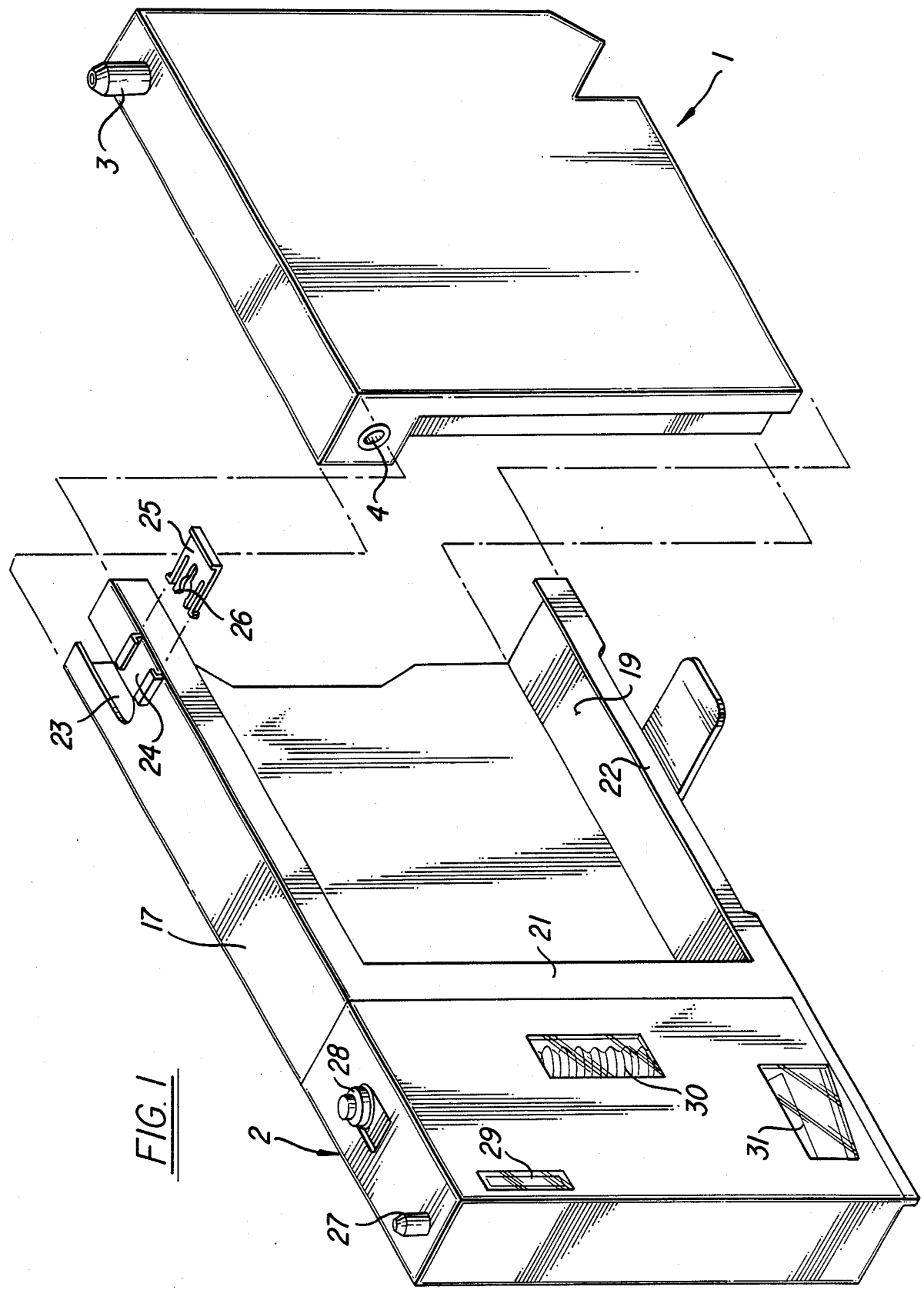

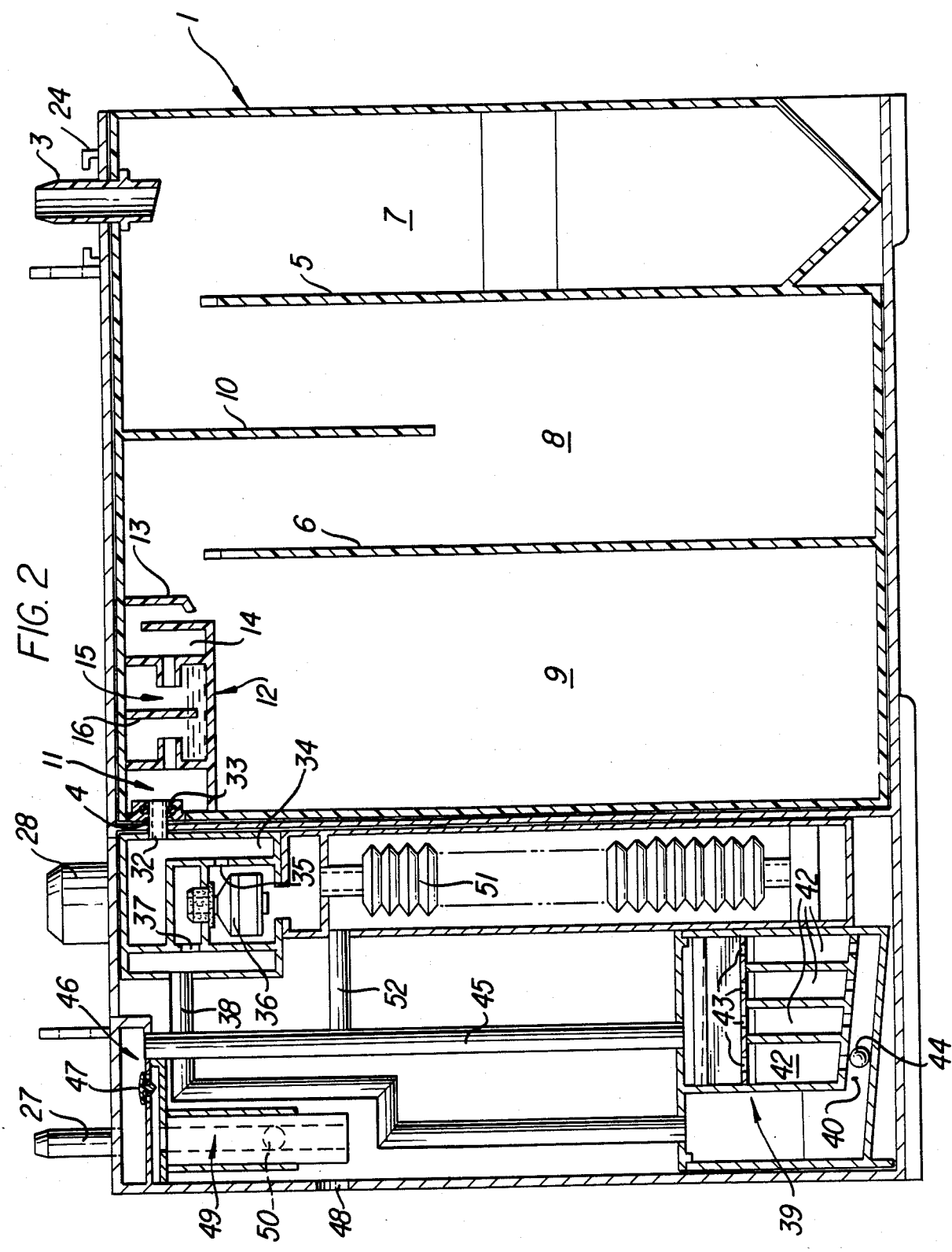

DRAINAGE DEVICE WITH DISPOSABLE COLLECTION CHAMBER

BACKGROUND OF THE INVENTION

The present invention relates to a drainage device including a disposable collection chamber and a nondisposable suction control chamber so that only the collection chamber need be discarded after use of the drainage device.

Chest drainage devices in which all of the operating parts are disposed within a single integral unit are well known in the art. U.S. Pat. No. 3,363,626 is an example of an early design of such a device. It is also known to construct thoracic drainage devices in separate modules so that a drainage device of a single or multiple bottles may be constructed. U.S. Pat. No. 3,847,152 is an example of such a device.

More recently, thoracic drainage devices have been provided with more complex internal elements to provide the physician with more information with regard to the patient's condition. Such drainage devices in many cases eliminate the need for partially filling certain of the chambers of the device with water prior to use. Typical of such dry drainage devices is that disclosed in U.S. Pat. No. 4,605,400 which discloses a device having valves to regulate the suction as well as to provide a one way valve means to prevent atmospheric air from entering the collection chamber. In addition, the device disclosed in U.S. Pat. No. 4,605,400 provides a bellows for indicating the respiration of the patient. Obviously, the additional structural elements provided in the drainage device shown in U.S. Pat. No. 4,605,400 substantially increases the cost of the drainage device and it has been necessary to consider modifying the device so as to decrease the cost to the patient substantially while still retaining the advantages of providing the physician with the diagnostic tools shown and described in U.S. Pat. No. 4,605,400.

There have been provided in the prior art a number of drainage device having collection chambers which may be disconnected from the remainder of the device. U.S. Pat. Nos. 4,439,190; 4,569,674 and 4,105,031 are typical of such devices. Such devices do not, however, provide a means for maintaining sterility of the operating elements of the drainage device in a separate nondisposable section with releasable locking means being provided between that section and a collection chamber which is provided with means for preventing liquids from flowing from the collection chamber into the nondisposable section of the apparatus.

SUMMARY OF THE INVENTION

The present invention provides a drainage device with two sections which may be attached together and locked in such position when in use. The collection chamber of the drainage device may be readily disconnected from the remainder of the unit and discarded after use while retaining the remaining elements of the drainage device in a nondisposable section. Means is provided in the collection chamber to prevent any infectious materials or liquid within the collection chamber from passing into the nondisposable section. There is provided a chamber in the nondisposable section of the drainage device for indicating the presence of liquid passing from the collection chamber into the nondisposable section of the drainage device.

An object of the present invention is to provide a drainage device with a nondisposable suction control chamber and a disposable collection chamber with means for releasably fastening the chambers together.

A further object of the present invention is to provide a drainage device with a nondisposable section containing suction control apparatus and means for preventing atmospheric air from passing into the collection chamber and a separable collection chamber provided with means for preventing contaminates from entering the suction control chamber.

Other objects and many of the attendant advantages of the present invention will become more readily apparent upon consideration of the following detailed specification when considered in connection with the accompanying drawings wherein:

BRIEF DESCRIPTION OF THE DRAWINGS

FIG. 1 is a perspective view of the two sections of the drainage device separated and;

FIG. 2 is a cross sectional view of the two sections of the drainage device when connected together.

DETAILED DESCRIPTION OF THE INVENTION

Referring now more specifically to the drawings wherein like numerals indicate like parts throughout the several views there is shown at 1 in FIG. 1 a collection chamber for a drainage device which is adapted to be attached to a nondisposable section 2 of the drainage device.

The collection chamber 1 has an inlet tube 3 mounted on the upper end thereof and this inlet is adapted to be connected to a thoracotomy tube which has the distal end thereof in communication with the pleural cavity of a patient. The collection chamber has an outlet passageway 4 which is adapted to provide a communicating passagseway between the collection chamber 1 and the operative elements of the drainage device within housing 2.

Referring to FIG. 2, the collection chamber 1 can be seen in section with upstanding partitions 5 and 6 which extend across the entire width of the collection chamber and extend from the bottom of the collection chamber to a point spaced below the upper end. Thus, it can be seen that a plurality of chambers 7, 8, and 9 are provided which are sequentially filled with liquid received from the inlet 3. Baffle 10 is provided which extends downwardly from the upper surface of the collection chamber and extends from one side of the collection chamber to the other. This baffle helps to limit movement of liquid within the chambers 7, 8 and 9 when the drainage device is moved.

At the end of collection chamber 1 in which the outlet 4 is located, there is provided a chamber 12 which performs two functions. Chamber 12 is designed to prevent liquid within the collection chamber 1 from spilling out through the outlet 4 into the nondisposable section 2 of the drainage device. In addition, the chamber 12 is provided with means to prevent any contaminates of infectious material such as bacteria from passing therethrough in the air stream into the nondisposable section 2.

The chamber 12 is provided with an inlet baffle 13 forming an inlet passageway into a telltale chamber 14. In the unlikely event that liquid from the collection chamber is carried into the inlet passageway formed by baffle 13 and over the partition separating the inlet passageway and telltale chamber 14, this liquid will be trapped in the telltale chamber 14. Adjacent the tell tale chamber 14, there is provided a liquid biocidal chamber 15. Within this biocidal chamber there is disposed a central partition 16 which extends downward from the top of the chamber and is provided with a passageway between the lower end of the partition and the bottom wall of the chamber. The chamber 15 contains approximately 2cc of glycerin which contains a biocide dissolved therein, such as, for example, povidone iodine, chlorhexidine gluconate, or a quaternary ammonium compound. The liquid trap removes particulates such as bacteria from the air stream, and the biocide kills any trapped organisms. It can be seen that any air from the collection chamber 1 passing through the outlet 4 into the nondisposable section 2 of the drainage device must bubble through the liquid biocidal chamber 15. The inlet and outlet passageways in the chamber 15 are short and do not allow liquid to enter the chamber even when the drainage device is tipped. The glycerin biocidal chamber has the characterististics of the chamber described in column 11 of U.S. Pat. No. 4,605,400 issued Aug. 12, 1986. It will be noted that there is provided an additional tell tale chamber 11 between the outlet from the chamber 15 and the outlet from the collection chamber. This tell tale chamber will indicate any liquid flow from the chamber 15.

Referring now more specifically to FIG. 1 it can be seen that the section 2 of the drainage device is provided with an outwardly extending top wall 17, sidewall 18 and bottom wall 19 together with flanges 20, 21 and 22 so as to receive the collection chamber 1 in sliding relationship therein. A slot 23 is formed at the end of top wall 17 and this slot receives the inlet tube 3 when the collection chamber 1 is slid into the space defined by walls 17, 18, 19 and flanges 20, 21 and 22. Locking means is provided to retain the inlet tube 3 within the slot 23. This locking means comprises a flanged plate 24 secured to the top wall 17 and adapted to receive a locking element 25 therein. The locking element 25 is provided with a recess 26 disposed between a pair of resilient fingers which receives the inlet tube 3.

The housing 2 is provided with an outlet 27 which may be connected with a suction source and is further provided with a high negativity relief valve 28. The details of construction of the high negativity relief valve 28 are fully disclosed in U.S. Pat. No. 4,605,400, FIGS. 6 to 8. Windows 29, 30 and 31 are provided on the front face of housing 2 so that the operation of the elements within the housing 2 may be observed.

The housing 2 is provided with an inlet tube 32 which is adapted to fit within the outlet 4 of the collection chamber 1. A rubber grommet 33 is provided in the outlet 4 to firmly seal the tube 32 within the inlet.

Immediately adjacent the inlet tube 32 in housing 2 there is provided a chamber 34 which is adapted to receive any liquid which flows through passageway 32. Any gas passing through passageway 32 will flow through opening 35 through oneway valve 36 and out through opening 37 into tube 38. The details of construction of oneway valve 36 are fully disclosed in U.S. Pat. No. 4,605,400. This device is designed to permit flow of gases from the collection chamber through the housing 2 and outwardly through the outlet tube 27 to the suction source but to prevent reverse flow of gases through the valve.

Gas passing through tube 38 flows when into air flow meter 39 which comprises a downwardly sloped passageway 40 having openings 41 therein and a plurality of passageways 42 extending upwardly to outlet openings 43. Glycerin or the like is disposed in the inclined passageway 40 and a ball 44 is disposed within the passageway. The device serves an as air flow meter in that at minimal air flow the glycerin and ball 44 will be forced downwardly in the inclined passageway only a sufficient amount to open one passageway 42 to the flow of air therethrough and with increased air flow additional passageways will be opened. Thus, the degree of leakage in the patient's pleural cavity can be readily observed through window 31 by determining the position of ball 44 within the inclined passage 40. The details of constructionn of the air flow meter are more fully described in U.S. Pat. No. 3,683,913, issued Aug. 15, 1972.

Air passing upwardly through the passageways 42 enters outlet tube 45 which terminates in suction control chamber 46. A suction control means such as a series of oneway valves 47 is provided within the suction control chamber 46 and these valves permit air entering through outlet to atmosphere 48 to pass upwardly and through the oneway valves 47 to maintain the appropriate suction within the collection chamber and the patient's pleural cavity. Air drawn from the pleural cavity through tube 45 and air passing from atmosphere 48 through suction control valves 47 passes outwardly through outlet to suction 27. The details of construction of the suction control chamber and the suction control valves is more fully disclosed in prior U.S. Pat. No. 4,605,400, issued Aug. 12, 1986.

There is further provided a pressure measuring means 49 comprising a passageway with a ball 50 disposed therein, the lower end of the passageway being open to a small bore in the bottom thereof and the amount of air passing upwardly through the bore determines the position of ball 50 in the passageway and therefore indicates the degree of negativity of the pressure measuring means are more fully disclosed in U.S. Pat. No. 4,605,400, issued Aug. 12, 1986. The pressure measuring means is disposed beneath below 29 in the front face of the drainage device so that the degree of negativity within the drainage device may be readily observed.

There is further provided a bellows 51 mounted in a chamber beneath the oneway valve 36. The interior of the bellows 51 is open to the pressure exisiting within the collection chamber and the outside of the bellows is subjected to the pressure within passageway 45 through connecting passageway 52. Thus, the bellows 51 will rise and fall with the breathing of the patient as more fully disclosed in U.S. Pat. No. 4,605,400. The respiration of the patient may be observed through the window 30 in the front face of the drainage device.

In operation the disposable section 1 of the drainage device is inserted within the housing 17 so that the outlet 4 from the section 1 is firmly engaged within the inlet tube 32 of the nondisposable section 2 of the drainage device. The suction tube 27 is connected with a suction source and the inlet 3 is connected via a thoracotomy tube with the pleural cavity of the patient. Liquid will flow from the pleural cavity through the inlet 3 into the collection chamber and will sequentially fill compartments 7, 8 and 9 of the collection chamber. In the event the drainage device is inadvertently tipped or moved about any liquid which may pass through the passageway adjacent baffle 13 will first be indicated in the telltale compartment 14. Under normal conditions any infectious material or contaminates in the air stream from the collection chamber into the nondisposable section will be removed in the biocidal glycerin bath as the entire air stream must bubble through the bath. In the event of extensive spillover liquid from the pleural cavity liquid may conceivably pass through liquid biocidal chamber 12 and into tell tale chamber 11. Liquid may pass through outlet 4 and into trap 34 in nondisposable section 2. In the letter event the nondisposable section 2 must be discarded along with the disposable collection chamber 1. However, if no liquid is disposed within chamber 34 the nondisposable portion of the unit may be resterilized and reused with only the collection chamber 1 being discarded. Obviously, the nondisposable section 2 contains all of the operative elements including the oneway valve 36 which performs the function of preventing atmospheric air from reaching the pleural cavity, the excess negativity relief valve 28, the respiratory measuring system 51, the suction control system 46, the air flow measuring meter 39 and the pressure measuring means 49. Thus, substantial savings may be effected by separating the collection chamber as a disposable unit from all of the operative elements of the drainage device.

Obviously many modifications and variations of the present invention are possible in light of the above teachings. What is claimed is new and is desired to be secured by Letters Patent is:

We claim:

1. A drainage device comprising a nondisposable section and a disposable section, said disposable section comprising a collection chamber, a patient tube inlet in said collection chamber, an outlet passageway in said collection chamber to be connected to said nondisposable section, said nondisposable section including an inlet adapted to be connected to the outlet passageway from said disposable section, a suction outlet in said nondisposable section, a passageway from said inlet in the nondisposable section to said suction outlet, valve means in said passageway to prevent atmospheric air from passing into the collection chamber, suction control means in said passageway for regulating the degree of suction applied to the collection chamber, means in said passageway including a fluid retaining chamber in said nondisposable section in fluid communication with the outlet from said collection chamber for determining whether fluid from the collection chamber has passed into said nondisposable section and means including baffles in said disposable section for preventing contaminates in said collection chamber from entering said nondisposable section.

2. A drainage device according to claim 1 and further including means for releasably locking said disposable and nondisposable sections together.

3. A drainage device according to claim 1 and further including means inn said passageway in said nondisposable section for measuring the respiration of a patient.

4. A drainage device according to claim 1 and further including means in said passageway in said nondisposable section for measuring the amount of air passing through the passageway from the collection chamber to the suction outlet.

5. A drainage device comprising a pair of sections adapted to be releasably locked together, one of said sections comprising a disposable collection chamber, said disposable collection chamber having an inlet adapted to be connected to a thoracotomy tube, an outlet from said collection chamber, partition means disposed in said collection chamber to prevent liquids from contacting said outlet, the other of said sections including a suction regulating chamber, an inlet to said other section for connection with the outlet from said collection chamber, a high negativity relief valve in said other section, and means disposed adjacent the inlet to said other section to indicate the passage of liquid from the collection chamber to said other section, said last named means including a fluid retaining chamber disposed immediately below the inlet to said other section.

6. A drainage device according to claim 5 and further including means for releasably locking said sections together.

7. A drainage device according to claim 5 and further including means for preventing atmospheric air passing into said collection chamber, said means being disposed in the other of said sections.

8. A collection chamber for a drainage device comprising a container, an inlet into said container, an outlet from said chamber, means for preventing contaminates from passing from within said container through the outlet, said means including a chamber with a biocidal bath in said chamber, said chamber being disposed adjacent the outlet to and chamber, said outlet adapted to be connected with a second chamber including suction regulating means and valve means to prevent atmospheric air from passing into said collection chamber and means in said second chamber including a fluid retaining chamber for determining whether fluid from the container has passed into said second chamber.

* * * * *